US012624129B2

(12) United States Patent
Mastrodonato et al.

(10) Patent No.: US 12,624,129 B2
(45) Date of Patent: May 12, 2026

(54) CROSSLINKED BUTYRATE OR BUTYRATE-FORMATE DERIVATIVES OF HYALURONIC ACID AND THE CROSSLINKING THEREOF

(71) Applicant: BMG PHARMA S.P.A., Milan (IT)

(72) Inventors: Marco Mastrodonato, Milan (IT); Luca Stucchi, Torviscosa (IT); Alessandra Sechi, Torviscosa (IT); Fabrizio Picotti, Torviscosa (IT); Rita Gianni, Monrupino (IT)

(73) Assignee: BMG PHARMA S.P.A., Torviscosa (IT)

( * ) Notice: Subject to any disclaimer, the term of this patent is extended or adjusted under 35 U.S.C. 154(b) by 905 days.

(21) Appl. No.: 17/756,119

(22) PCT Filed: Nov. 19, 2020

(86) PCT No.: PCT/IB2020/060888
§ 371 (c)(1),
(2) Date: May 18, 2022

(87) PCT Pub. No.: WO2021/099977
PCT Pub. Date: May 27, 2021

(65) Prior Publication Data

US 2022/0411541 A1 Dec. 29, 2022

(30) Foreign Application Priority Data

Nov. 20, 2019 (IT) ........................ 102019000021693

(51) Int. Cl.

| | |
|---|---|
| ***C08B 37/08*** | (2006.01) |
| ***A61K 8/73*** | (2006.01) |
| ***A61K 31/167*** | (2006.01) |
| ***A61K 47/61*** | (2017.01) |
| ***A61Q 19/00*** | (2006.01) |

(52) U.S. Cl.
CPC .......... *C08B 37/0072* (2013.01); *A61K 8/735* (2013.01); *A61K 31/167* (2013.01); *A61K 47/61* (2017.08); *A61Q 19/00* (2013.01)

(58) Field of Classification Search
CPC .. C08B 37/0072; A61K 8/735; A61K 31/167; A61K 47/61; A61Q 19/00
See application file for complete search history.

(56) References Cited

U.S. PATENT DOCUMENTS

| | | | | |
|---|---|---|---|---|
| 4,303,676 A * | 12/1981 | Balazs | ..................... | A61K 8/64 514/777 |
| 2010/0226988 A1 | 9/2010 | Lebreton | | |
| 2010/0292459 A1 | 11/2010 | Stucchi et al. | | |

FOREIGN PATENT DOCUMENTS

| | | | | |
|---|---|---|---|---|
| CN | 110237054 A | 9/2019 | | |
| EP | 0341745 A1 | 11/1989 | | |
| JP | 2010077434 A | 4/2010 | | |
| JP | 2010514878 A | 5/2010 | | |
| JP | 2013544583 A | 12/2013 | | |
| WO | WO1989010941 A1 * | 11/1986 | ............. | C08B 15/00 |
| WO | 1997049412 A1 | 12/1997 | | |
| WO | 2012062775 A1 | 5/2012 | | |
| WO | WO-2024026078 A1 * | 2/2024 | ............. | C08B 31/04 |

OTHER PUBLICATIONS

Search Report and Written Opinion of PCT/IB2020/060888 of Feb. 8, 2021.
Letter reporting office action issued Nov. 11, 2024 in counterpart Japanese Patent Application No. 2022-529349.
Office Action issued Nov. 11, 2024 in counterpart Japanese Patent Application No. 2022-529349.

* cited by examiner

*Primary Examiner* — Andrea Olson
*Assistant Examiner* — Benjamin M Brandsen
(74) *Attorney, Agent, or Firm* — Silvia Salvadori, P.C.; Silvia Salvadori

(57) ABSTRACT

The present invention relates to a process for the preparation of crosslinked hyaluronic acid butyrate or crosslinked hyaluronic acid butyrate-formate or an acceptable salt thereof, wherein the process comprises the crosslinking reaction of hyaluronic acid butyrate or hyaluronic acid butyrate-formate or a pharmaceutically acceptable salt thereof in an organic solvent with a carboxyl activating reagent, characterized in that the hyaluronic acid butyrate or hyaluronic acid butyrate-formate or pharmaceutically acceptable salt thereof is a mixture of a high-molecular-weight polysaccharide and a low-molecular-weight polysaccharide.

21 Claims, No Drawings

CROSSLINKED BUTYRATE OR BUTYRATE-FORMATE DERIVATIVES OF HYALURONIC ACID AND THE CROSSLINKING THEREOF

This application is a U.S. national stage of PCT/IB2020/060888 filed on 19 Nov. 2020, which claims priority to and the benefit of Italian Patent Application No. 102019000021693 filed on 20 Nov. 2019, the contents of which are incorporated herein by reference in their entireties.

The present invention relates to a process for the preparation of crosslinked hyaluronic acid butyrate or crosslinked hyaluronic acid butyrate-formate or a salt thereof, the product obtained by said process, and its formulation for pharmaceutical or cosmetic use or as a medical device.

In particular, the present invention relates to crosslinking of a combination of different molecular weights of hyaluronic acid butyrate or hyaluronic acid butyrate-formate or a salt thereof which surprisingly gives rise to a polymer with a different rheological profile from that of a polymer obtained by combining the same polymers, previously crosslinked.

The crosslinked butyric-formic esters of hyaluronic acid prepared by said process have better viscoelastic properties than gels obtained by combining polysaccharides with different molecular weights previously crosslinked, and can therefore be advantageously used in the pharmaceutical and dermocosmetic fields and as medical devices, in particular as injectables.

STATE OF THE ART

Hyaluronic acid is a glycosaminoglycan consisting of repeating units of glucuronic acid and N-acetylglucosamine bonded together or, alternatively, via glycoside bonds $\beta1\rightarrow4$ and $\beta1\rightarrow3$. Hyaluronic acid is an essential element of connective tissue, and is also present in synovial fluid, vitreous humour and umbilical cord.

WO98/23648 discloses the preparation of hyaluronic acid butyrate (SHB) wherein the hydroxyl groups of hyaluronic acid are esterified with butyric acid residues. Hyaluronic acid butyrate has anti-inflammatory, anti-proliferative and skin-protecting properties as a skin elasticiser and moisturizer.

WO2009/068215 discloses the preparation of mixed butyric-formic esters of hyaluronic acid and their use in dermocosmetics, with skin-protecting and anti-inflammatory activity. The mixed esters are prepared with butyric anhydride and formamide (FA), with N,N-dimethylamino pyridine (N,N-DMAP) as basic catalyst.

EP 341745 discloses the preparation of autocrosslinked hyaluronic acid starting with hyaluronic acid or hyaluronic acid wherein the carboxyl groups are partly esterified with various types of alcohols. The carboxyl function of hyaluronic acid (or of the ester derivatives thereof, defined as "external esters") is involved in the formation of intra- or intermolecular esters with the alcohol hydroxyls of the repeating units of hyaluronic acid, with consequent crosslinking (defined as "autocrosslinking").

WO2008/081255 discloses the preparation of autocrosslinked hyaluronic acid characterized by the concomitant presence of esters with non-polysaccharide carboxylic acids, including butyric-formic acid, and esters between the acid group and the alcohol groups of the initial polysaccharide with crosslinking between the polysaccharide chains.

EP 2614090 discloses cooperative hybrid complexes between low-molecular-weight and high-molecular-weight hyaluronic acid, wherein the hyaluronic acid molecules in solution are characterized by cooperative interaction based on the formation of hydrophobic bonds and intra- and inter-chain hydrogen bonds, the extent of which depends on the molecular weight of the polysaccharide.

It has now been discovered that crosslinking hyaluronic acid butyrate or hyaluronic acid butyrate-formate with different molecular weights increases the chemical and biological stability of the polysaccharide, at the same time providing an improved rheological profile, which is particularly advantageous for applications in the pharmaceutical and dermocosmetic fields and as a medical device, in particular as an injectable.

DESCRIPTION OF THE INVENTION

The object of the present invention is a process for the preparation of crosslinked hyaluronic acid butyrate or crosslinked hyaluronic acid butyrate-formate or an acceptable salt thereof, wherein the process comprises the reaction of hyaluronic acid butyrate or hyaluronic acid butyrate-formate or a pharmaceutically acceptable salt thereof in an organic solvent with a carboxyl group activating reagent and a base, characterized in that the hyaluronic acid butyrate or hyaluronic acid butyrate-formate or pharmaceutically acceptable salt thereof is a mixture of a high-molecular-weight polysaccharide having a weight-average molecular weight ranging from 1000 kDa to 10000 kDa, preferably from 1000 kDa to 6000 kDa, and more preferably from 1000 kDa to 2000 kDa, and a low-molecular-weight polysaccharide having a weight-average molecular weight ranging from 1 kDa to 900 kDa, preferably from 10 kDa to 500 kDa, and more preferably from 50 kDa to 300 kDa.

The degree of substitution (DS), defined as the ratio between the number of butyric or butyric-formic acid residues per GlcNAc-GlcUA disaccharide unit of hyaluronic acid, can range, for example, between 0.1 and 2.2.

The high-molecular-weight polysaccharide and the low-molecular-weight polysaccharide are preferably used in a ratio ranging from 80:20 to 20:80 by weight.

"Acceptable salt" here means a salt acceptable for pharmaceutical or cosmetic use or in medical devices, such as the sodium, potassium, lithium or quaternary ammonium salt, for example tetrabutylammonium, preferably the sodium salt.

The crosslinking reaction is preferably conducted in an organic solvent selected from polar aprotic organic solvents such as N,N-dimethylformamide, dimethylacetamide, dimethylsulphoxide, N-methylpyrrolidone or formamide. The preferred solvent is formamide.

The carboxyl group activating reagent is preferably selected from the group consisting of carbonyldiimidazole, 1,1'-carbonyl-di-(1,2,4-triazole), 1,1'-oxalylimidazole, 1,1'-thiocarbonylimidazole, 1,1'-carbonyl bis(2-methylimidazole), N-hydroxysuccinimide, p-nitrophenol, p-nitrophenyltrifluoroacetate, 2-halo-N-alkylpyridine salts and acyl halides. More preferably, the carboxyl group activating reagent is carbonyldiimidazole.

The base used in the crosslinking reaction is preferably selected from inorganic bases such as carbonates, bicarbonates or hydroxides of an alkali or alkaline-earth metal, in particular sodium, potassium or magnesium, aromatic or aliphatic organic bases comprising at least one trisubstituted nitrogen atom such as pyridine or the homologues thereof, such as collidine, or basic amines such as triethylamine, imidazole, N-methyl-piperazine or dimethylaminopyridine, or the alkali or alkaline-earth metal salt of an organic acid, such as sodium or potassium acetate. More preferably the base used is sodium carbonate or dimethylaminopyridine.

The reaction mixture is preferably maintained at a temperature ranging between 20° C. and 30° C. for between 4 and 24 h.

When the reaction is complete, the mixture is diluted with water and the product is recovered by precipitation in a suitable solvent. The product thus obtained is then purified, for example by successive washes with suitable solvents and filtration.

The mixture of the high-molecular-weight and low-molecular-weight derivative of hyaluronic acid (hyaluronic acid butyrate or hyaluronic acid butyrate-formate or a salt thereof) used in the crosslinking reaction can be produced by mixing the high-molecular-weight hyaluronic acid derivative with the low-molecular-weight derivative thereof or conducting the derivatisation reaction with butyric acid or butyric acid and formamide on a mixture of high-molecular-weight and low-molecular-weight hyaluronic acid.

A further object of the present invention is crosslinked hyaluronic acid butyrate or crosslinked hyaluronic acid butyrate-formate or a pharmaceutically acceptable salt thereof obtained by the process described above.

The crosslinked polysaccharides obtained by said process have a different rheological profile from those obtained by combining the same starting polysaccharides, previously crosslinked.

The rheological profile of the crosslinked polysaccharides according to the invention is characterized by high viscosity and higher modulus of elasticity (G') and viscosity (G") values. In particular the crosslinked polysaccharides according to the invention obtained by crosslinking the mixture of high-molecular-weight and low-molecular-weight polysaccharide possess greater viscosity and a higher modulus of elasticity (G') and viscosity (G") than the mixture of crosslinked high-molecular-weight polysaccharide and crosslinked low-molecular-weight polysaccharide.

Moreover, the presence of polysaccharides with different molecular weights gives rise not only to the typical biological properties of high-molecular-weight sodium hyaluronate, such as proliferative activity in the cells that make up the extracellular matrix and anti-inflammatory activity, but also to those typical of low-molecular-weight sodium hyaluronate, such as angiogenic activity and modulation of the inflammatory processes, giving a unique profile of biological activity while still maintaining the biocompatibility typical of hyaluronic acid.

Finally, the crosslinked polysaccharides obtained by the process according to the invention exhibit improved resistance to enzymatic degradation, which promotes a long-lasting activity in vivo.

A further object of the present invention is pharmaceutical or cosmetic formulations or medical devices comprising crosslinked hyaluronic acid butyrate or crosslinked hyaluronic acid butyrate-formate or a pharmaceutically acceptable salt thereof obtained by the process described above, and at least one pharmaceutically or cosmetically acceptable excipient and/or carrier.

The pharmaceutical or cosmetic formulation or medical device can also contain a local anaesthetic such as lidocaine.

The cosmetic formulations can be used for dermocosmetic anti-aging or revitalizing treatments and in mesotherapy applications.

The pharmaceutical formulations or medical devices can be used in the topical treatment of skin lesions and rashes and ophthalmic lesions.

A further object of the invention is medical devices usable as adjuvants for ophthalmic application, for example in eye surgery or treatment of dry eye, or as adjuvants in the treatment of osteoarthritis or as dermal fillers.

The hyaluronic acid butyric-formate ester is prepared as disclosed in WO2009/068215, and the hyaluronic acid butyric ester is prepared as disclosed in WO2016/113192.

Crosslinked hyaluronic acid butyrate or crosslinked hyaluronic acid butyrate-formate or a salt thereof obtained by the process reported above possess considerable anti-irritant, anti-inflammatory and antioxidant activities which influence the acute inflammatory response. Due to said characteristic, the crosslinked polysaccharides according to the invention are particularly indicated for injectable, dermocosmetic or intra-articular application, in cases where acute inflammation caused by subcutaneous injection or inflammation correlated with osteoarthritis constitutes a problematic target.

EXAMPLES

Methods

Instrumentation Used:

- VARIAN VNMR 500 MHz spectrometer equipped with a 5 mm multinuclear reverse probe with a z gradient for determination of the degree of substitution (DS);
- Anton Paar MCR 301 rheometer equipped with parallel plates (diameter 25 mm, satin-finish) thermostated to 25° C.

Determination of Degree of Substitution (DS)

The degree of substitution in butyrate esters on the hyaluronic acid derivative was quantitated by NMR spectroscopy. The $^{1}H$ NMR spectra were effected in $D_2O$ with a VARIAN VNMR 500 MHz spectrometer equipped with a 5 mm multinuclear reverse probe with a z gradient. The tests were conducted by thermostating the measurement probe to 298° K.

The quantitation of DS in butyrate ester was performed after exhaustive hydrolysis with NaOD directly in the NMR tube.

The $^{1}H$ NMR spectrum of the hydrolysate allows integration of the signals attributable to butyric acid (vicinal methyl and methylene protons) and those attributable to hyaluronic acid (saccharide protons, excluding the two anomeric protons); their ratio determines the degree of substitution.

Determination of Elastic and Viscous Moduli by Rheology Testing.

The rheology testing of the gels was conducted with an Anton Paar MCR 301 rheometer equipped with parallel plates (diameter 25 mm, satin-finish) thermostated to 25° C. The measurements were conducted on samples swollen in ultra-pure water at the concentration of 1% w/v, 24 h after mixing.

The mechanical spectrum was recorded for each gel in oscillation mode (stress sweep) at a constant frequency of 1 Hz, which allowed the determination of modulus of elasticity G' and modulus of viscosity G" (unit of measurement Pa); for some gels the flow curve, which measures viscosity $\eta$ (unit of measurement Pa*s) on variation of the force applied, was also recorded.

Example 1: Synthesis of Sodium Hyaluronate Butyrate-Formate (MW: 1500 kDa; $DS_{but}$:0.3; $DS_{for}$:0.01)

100 ml of formamide was introduced into a 1 l reactor, followed by 5.0 g of sodium hyaluronate with a molecular weight of 1500 kDa. The mixture was thermostated to 95° C. and maintained under stirring at a constant temperature for 1.5 h, until the polymer had completely dissolved. The temperature was then reduced to 25° C., and the mixture was maintained under stirring overnight.

Sodium carbonate ($Na_2CO_3$— 262.0 mg) was then added, followed in sequence by butyryl-imidazolide (1.1 g) after 0.5 h. The mixture was left under stirring for 1.5 h at 25° C. The reaction was quenched with 50 ml of acidic water, and the product was isolated by precipitation with acetone and subsequent filtration.

The crude reaction product was purified by several washes with acetone and methanol, each followed by vacuum filtration. The precipitate was dried under vacuum at a temperature ≤60° C. for about 24 h.

10 mg of sample was solubilised in 0.9 ml of heavy water ($D_2O$) and transferred to an NMR test tube.

After hydrolysis of the butyric-formic esters by adding NaOD (deuterated sodium hydroxide), the NMR spectra exhibited a DS of 0.3 in butyric acid and a DS of 0.01 in formic acid.

Example 2: Synthesis of Sodium Hyaluronate Butyrate-Formate (MW: 1500 kDa; $DS_{but}$:0.95; $DS_{for}$:0.01)

150 ml of formamide was introduced into a 1 l reactor, followed by 7.5 g of sodium hyaluronate with a molecular weight of 1500 kDa. The mixture was thermostated to 95° C. and maintained under stirring at a constant temperature for 1.5 h, until the polymer had completely dissolved. The temperature was then reduced to 25° C., and the mixture was maintained under stirring overnight.

Sodium carbonate ($Na_2CO_3$— 600 mg) was then added, followed in sequence by butyryl-imidazolide (6.7 g) after 0.5 h. The mixture was left under stirring for 1.5 h at 25° C. The reaction was quenched with 65 ml of acidic water, and the product was isolated by precipitation with acetone and subsequent filtration.

The crude reaction product was purified by several washes with acetone and methanol, each followed by vacuum filtration. The precipitate was dried under vacuum at a temperature ≤60° C. for about 24 h.

10 mg of sample was solubilised in 0.9 ml of heavy water ($D_2O$) and transferred to an NMR test tube.

After hydrolysis of the butyric-formic esters by adding NaOD (deuterated sodium hydroxide), the NMR spectra exhibited a DS of 0.95 in butyric acid and 0.01 in formic acid.

Example 3: Synthesis of Sodium Hyaluronate Butyrate-Formate (MW: 1500 kDa; $DS_{but}$:1.6; $DS_{for}$:0.03)

200 ml of formamide was introduced into a 1 l reactor, followed by 10.15 g of HANa with a molecular weight of 1500 kDa. The mixture was thermostated to 95° C. and maintained under stirring at a constant temperature for 1 h, until the polymer had completely dissolved. The temperature was then reduced to 25° C., and the mixture was maintained under stirring overnight.

Sodium carbonate ($Na_2CO_3$— 2.7 g) was then added, followed in sequence by butyryl-imidazolide (26.2 g) after 0.5 h. The mixture was left under stirring for 1.5 h at 25° C. The reaction was quenched with 200 ml of acidic water, and the product was isolated by precipitation with acetone and subsequent decanting.

The crude reaction product was purified by several washes with acetone and methanol, each followed by vacuum filtration. The precipitate was dried under vacuum at a temperature ≤60° C. for about 16 h.

10 mg of sample was solubilised in 0.9 ml of heavy water ($D_2O$) and transferred to an NMR test tube.

After hydrolysis of the butyric-formic esters by adding NaOD (deuterated sodium hydroxide), the NMR spectra exhibited a DS of 1.6 in butyric acid and 0.03 in formic acid.

Example 4: Synthesis of Sodium Hyaluronate Butyrate-Formate (MW: 300 kDa; $DS_{but}$:0.3; $DS_{for}$:0.02)

2.67 l of formamide was introduced into a 15 l reactor, followed by 200.5 g of sodium hyaluronate with a molecular weight of 300 kDa. The mixture was thermostated to 95° C. and maintained under stirring at a constant temperature for 1.5 h, until the polymer had completely dissolved. The temperature was then reduced to 25° C., and the mixture was maintained under stirring overnight.

Sodium carbonate ($Na_2CO_3$— 10.57 g) was then added, followed in sequence by butyryl-imidazolide (36.81 g) after 0.5 h. The mixture was left under stirring for 1.5 h at 25° C. The reaction was quenched with 1.381 of acidic water, and the product was isolated by precipitation with acetone and subsequent decanting.

The crude reaction product was purified by several washes with acetone and methanol, each followed by vacuum filtration. The precipitate was dried under vacuum at a temperature ≤60° C. for about 16 h.

10 mg of sample was solubilised in 0.9 ml of heavy water ($D_2O$) and transferred to an NMR test tube.

After hydrolysis of the butyric-formic esters by adding NaOD (deuterated sodium hydroxide), the NMR spectra exhibited a DS of 0.3 in butyric acid and 0.02 in formic acid.

Example 5: Synthesis of Sodium Hyaluronate Butyrate-Formate (MW: 300 kDa; $DS_{but}$:0.95; $DS_{for}$:0.01)

80 ml of formamide was introduced into a 1 l reactor, followed by 6 g of sodium hyaluronate with a molecular weight of 300 kDa. The mixture was thermostated to 95° C. and maintained under stirring at a constant temperature for 1.5 h, until the polymer had completely dissolved. The temperature was then reduced to 25° C.

Sodium carbonate ($Na_2CO_3$— 480 mg) was then added, followed in sequence by butyryl-imidazolide (4.2 g) after 0.5 h. The mixture was left under stirring for 1.5 h at 25° C. The reaction was quenched with 40 ml of acidic water, and the product was isolated by precipitation with acetone and subsequent filtration.

The crude reaction product was purified by several washes with acetone and methanol, each followed by vacuum filtration. The precipitate was dried under vacuum at a temperature ≤60° C. for about 24 h.

10 mg of sample was solubilised in 0.9 ml of heavy water ($D_2O$) and transferred to an NMR test tube.

After hydrolysis of the butyric-formic esters by adding NaOD (deuterated sodium hydroxide), the NMR spectra exhibited a DS of 0.95 in butyric acid and 0.01 in formic acid.

Example 6: Synthesis of Sodium Hyaluronate Butyrate-Formate (MW: 300 kDa; $DS_{but}$:2.16; $DS_{for}$:0.02)

50 ml of formamide was introduced into an 0.5 l flask, followed by 5 g of sodium hyaluronate with a molecular weight of 300 kDa. The mixture was thermostated to 95° C. and maintained under stirring at a constant temperature for 1.5 h, until the polymer had completely dissolved. The temperature was then reduced to 25° C., and the system was maintained under stirring overnight.

Sodium carbonate ($Na_2CO_3$— 1.34 g) was then added, followed in sequence by butyryl-imidazolide (18.41 g) after 0.5 h. The mixture was left under stirring for 1.5 h at 25° C. The reaction was quenched with 70 ml of acidic water, and the product was isolated by precipitation with acetone and subsequent filtration.

The crude reaction product was purified by several washes with acetone and methanol, each followed by vacuum filtration. The precipitate was dried under vacuum at a temperature ≤60° C. for about 24 h.

10 mg of sample was solubilised in 0.9 ml of heavy water ($D_2O$) and transferred to an NMR test tube.

After hydrolysis of the butyric-formic esters by adding NaOD (deuterated sodium hydroxide), the NMR spectra exhibited a DS of 2.16 in butyric acid and 0.02 in formic acid.

Example 7: Synthesis of Sodium Hyaluronate Butyrate (MW: 25 kDa; $DS_{but}$:0.35)

25 ml of water was introduced into an 0.5 l flask, followed by 5 g of sodium hyaluronate with a molecular weight of 25 kDa. The mixture was thermostated to 25° C. and maintained under stirring at a constant temperature for 1.5 h, until the polymer had completely dissolved.

Sodium carbonate ($Na_2CO_3$— 0.8 g) was then added, followed in sequence by butyryl-imidazolide (0.9 g) after 0.5 h. The mixture was left under stirring for 1.0 h at 25° C. The reaction was quenched with 5 ml of acidic water, and the product was isolated by precipitation with isopropanol and subsequent filtration.

The crude reaction product was purified by several washes with isopropanol and water, each followed by vacuum filtration. The precipitate was dried under vacuum at 25° C. for about 48 h.

10 mg of sample was solubilised in 0.9 ml of heavy water ($D_2O$) and transferred to an NMR test tube.

After hydrolysis of the butyric esters by adding NaOD (deuterated sodium hydroxide), the NMR spectra exhibited a DS of 0.35 in butyric acid.

Example 8: Synthesis of Sodium Hyaluronate Butyrate (MW: 25 kDa; $DS_{but}$:0.9)

25 ml of water was introduced into an 0.5 l flask, followed by 5 g of sodium hyaluronate with a molecular weight of 25 kDa. The mixture was thermostated to 25° C. and maintained under stirring at a constant temperature for 1.5 h, until the polymer had completely dissolved.

Sodium carbonate ($Na_2CO_3$— 4.0 g) was then added, followed in sequence by butyryl-imidazolide (2.5 g) after 0.5 h. The mixture was left under stirring for 1.0 h at 25° C. The reaction was quenched with 20 ml of acidic water, and the product was isolated by precipitation with isopropanol and subsequent filtration.

The crude reaction product was purified by several washes with isopropanol and water, each followed by vacuum filtration. The precipitate was dried under vacuum at 25° C. for about 48 h.

10 mg of sample was solubilised in 0.9 ml of heavy water ($D_2O$) and transferred to an NMR test tube.

After hydrolysis of the butyric esters by adding NaOD (deuterated sodium hydroxide), the NMR spectra exhibited a DS of 0.9 in butyric acid.

Example 9: Synthesis of Sodium Hyaluronate Butyrate (MW: 25 kDa; $DS_{but}$:1.6)

35 ml of water was introduced into an 0.5 l flask, followed by 5 g of sodium hyaluronate with a molecular weight of 25 kDa. The mixture was thermostated to 25° C. and maintained under stirring at a constant temperature for 1.5 h, until the polymer had completely dissolved.

Sodium carbonate ($Na_2CO_3$— 6.61 g) was then added, followed in sequence by butyryl-imidazolide (11.9 g) after 0.5 h. The mixture was left under stirring for 1.0 h at 25° C. The reaction was quenched with 20 ml of acidic water, and the product was isolated by precipitation with isopropanol and subsequent filtration.

The crude reaction product was purified by several washes with isopropanol and water, each followed by vacuum filtration. The precipitate was dried under vacuum at 25° C. for about 48 h.

10 mg of sample was solubilised in 0.9 ml of heavy water ($D_2O$) and transferred to an NMR test tube.

After hydrolysis of the butyric esters by adding NaOD (deuterated sodium hydroxide), the NMR spectra exhibited a DS of 1.6 in butyric acid.

Example 10: Synthesis of Crosslinked Sodium Hyaluronate Butyrate-Formate (80:20; MW: 1500 kDa; $DS_{but}$:1.6; $DS_{for}$:0.03: MW: 300 kDa; $DS_{but}$:0.3; $DS_{for}$:0.02)

20 ml of formamide was introduced into a 100 ml three-necked flask, followed by 0.8 g of the product obtained in Example 3 and 0.2 g of the product obtained in Example 4. The mixture was thermostated to 95° C. and maintained under stirring at a constant temperature for 2.5 h, until the polymers had completely dissolved.

The temperature was then reduced to 25° C., and the system was maintained under stirring overnight.

Sodium carbonate ($Na_2CO_3$— 60 mg) was added, followed by CDI (300 mg dissolved in 1.2 ml of DMSO) after 0.5 h. The mixture was left under stirring for 24 h at 25° C.

The reaction was quenched by adding 40 ml of water, and the product was isolated by precipitation in acetone and subsequent decanting.

The crude reaction product was purified by several washes with acetone and methanol, each followed by vacuum filtration. The precipitate was dried under vacuum at room temperature for about 16 h.

50 mg of sample was added to 5 ml of ultra-pure water (concentration 1% w/v); 24 h after mixing, the resulting gel, on rheology testing, gave G'=1550 Pa and G"=186 Pa.

Example 11: Synthesis of Crosslinked Sodium Hyaluronate Butyrate-Formate (50:50; MW: 1500 kDa; $DS_{but}$:1.6; $DS_{for}$:0.03: MW: 300 kDa; $DS_{but}$:0.3; $DS_{for}$:0.02)

20 ml of formamide was introduced into a 100 ml three-necked flask, followed by 0.5 g of the product obtained in Example 3 and 0.5 g of the product obtained in Example 4. The mixture was thermostated to 95° C. and maintained under stirring at a constant temperature for 2.5 h, until the polymers had completely dissolved.

The temperature was then reduced to 25° C., and the system was maintained under stirring overnight.

Sodium carbonate ($Na_2CO_3$— 60 mg) was added, followed by CDI (300 mg dissolved in 1.2 ml of DMSO) after 0.5 h. The mixture was left under stirring for 24 h at 25° C.

The reaction was quenched by adding 40 ml of water, and the product was isolated by precipitation in acetone and subsequent decanting.

The crude reaction product was purified by several washes with acetone and methanol, each followed by vacuum filtration. The precipitate was dried under vacuum at room temperature for about 16 h.

50 mg of sample was added to 5 ml of ultra-pure water (concentration 1% w/v); 24 h after mixing, the resulting gel, on rheology testing, gave G'=73 Pa and G"=16 Pa.

Example 12: Synthesis of Crosslinked Sodium Hyaluronate Butyrate-Formate (20:80; MW: 1500 kDa; $DS_{but}$:1.6; $DS_{for}$:0.03: MW: 300 kDa; $DS_{but}$:0.3; $DS_{for}$:0.02)

20 ml of formamide was introduced into a 100 ml three-necked flask, followed by 0.2 g of the product obtained in Example 3 and 0.8 g of the product obtained in Example 4. The mixture was thermostated to 95° C. and maintained under stirring at a constant temperature for 2.5 h, until the polymers had completely dissolved.

The temperature was then reduced to 25° C., and the system was maintained under stirring overnight.

Sodium carbonate ($Na_2CO_3$— 73 mg) was added, followed by CDI (345 mg dissolved in 1.4 ml of DMSO) after 0.5 h. The mixture was left under stirring for 24 h at 25° C.

The reaction was quenched by adding 40 ml of water, and the product was isolated by precipitation in acetone and subsequent decanting.

The crude reaction product was purified by several washes with acetone and methanol, each followed by vacuum filtration. The precipitate was dried under vacuum at room temperature for about 5 h.

Example 13: Synthesis of Crosslinked Sodium Hyaluronate Butyrate-Formate (80:20; MW: 1500 kDa; $DS_{but}$:0.95; $DS_{for}$:0.01: MW: 300 kDa; $DS_{but}$:0.95; $DS_{for}$:0.01)

20 ml of formamide was introduced into a 100 ml three-necked flask, followed by 0.8 g of the product obtained in Example 2 and 0.2 g of the product obtained in Example 5. The mixture was thermostated to 95° C. and maintained under stirring at a constant temperature for 2.5 h, until the polymers had completely dissolved. The temperature was then reduced to 25° C., and the system was maintained under stirring overnight.

Sodium carbonate ($Na_2CO_3$— 60 mg) was then added, followed by CDI (340 mg dissolved in 1.4 ml of DMSO) after 0.5 h. The mixture was left under stirring for 24 h at 25° C.

The reaction was quenched by adding 40 ml of water, and the product was isolated by precipitation in acetone and subsequent decanting.

The crude reaction product was purified by several washes with acetone and methanol, each followed by vacuum filtration. The precipitate was dried under vacuum at room temperature for about 16 h.

Example 14: Synthesis of Crosslinked Sodium Hyaluronate Butyrate-Formate (80:20; MW: 25 kDa; $DS_{but}$:0.9: MW: 1500 kDa; $DS_{but}$: 0.95; $DS_{for}$:0.01)

20 ml of formamide was introduced into a 100 ml three-necked flask, followed by 0.8 g of the product obtained in Example 8 and 0.2 g of the product obtained in Example 2. The mixture was thermostated to 95° C. and maintained under stirring at a constant temperature for 2.5 h, until the polymers had completely dissolved. The temperature was then reduced to 25° C., and the system was maintained under stirring overnight.

Sodium carbonate ($Na_2CO_3$— 65 mg) was then added, followed by CDI (345 mg dissolved in 1.4 ml of DMSO) after 0.5 h. The mixture was left under stirring for 24 h at 25° C.

The reaction was quenched by adding 40 ml of water, and the product was isolated by precipitation in acetone and subsequent decanting.

The crude reaction product was purified by several washes with acetone and methanol, each followed by vacuum filtration. The precipitate was dried under vacuum at room temperature for about 16 h.

Example 15: Synthesis of Crosslinked Sodium Hyaluronate Butyrate-Formate (20:80; MW: 25 kDa; $DS_{but}$:0.9: MW: 1500 kDa; $DS_{but}$: 0.95; $DS_{for}$:–0.01)

20 ml of formamide was introduced into a 100 ml three-necked flask, followed by 0.2 g of the product obtained in Example 8 and 0.8 g of the product obtained in Example 2. The mixture was thermostated to 95° C. and maintained under stirring at a constant temperature for 2.5 h, until the polymers had completely dissolved. The temperature was then reduced to 25° C., and the system was maintained under stirring overnight.

Sodium carbonate ($Na_2CO_3$— 70 mg) was then added, followed by CDI (348 mg dissolved in 1.4 ml of DMSO) after 0.5 h. The mixture was left under stirring for 24 h at 25° C.

The reaction was quenched by adding 40 ml of water, and the product was isolated by precipitation in acetone and subsequent decanting.

The crude reaction product was purified by several washes with acetone and methanol, each followed by vacuum filtration. The precipitate was dried under vacuum at room temperature for about 16 h.

Example 16: Synthesis of Crosslinked Sodium Hyaluronate Butyrate-Formate (80:20; MW: 25 kDa; $DS_{but}$:0.35: MW: 1500 kDa; $DS_{but}$: 1.6; $DS_{for}$:0.03)

20 ml of formamide was introduced into a 100 ml three-necked flask, followed by 0.8 g of the product obtained in Example 7 and 0.2 g of the product obtained in Example 3. The mixture was thermostated to 95° C. and maintained under stirring at a constant temperature for 2.5 h, until the polymers had completely dissolved. The temperature was then reduced to 25° C., and the system was maintained under stirring overnight.

Sodium carbonate ($Na_2CO_3$— 78 mg) was then added, followed by CDI (360 mg dissolved in 1.3 ml of DMSO) after 0.5 h. The mixture was left under stirring for 24 h at 25° C.

The reaction was quenched by adding 40 ml of water, and the product was isolated by precipitation in acetone and subsequent decanting.

The crude reaction product was purified by several washes with acetone and methanol, each followed by vacuum filtration. The precipitate was dried under vacuum at room temperature for about 18 h.

Example 17: Synthesis of Crosslinked Sodium Hyaluronate Butyrate-Formate (20:80; MW: 25 kDa; $DS_{but}$:0.35: MW: 1500 kDa; $DS_{but}$: 1.6; $DS_{for}$:0.03)

20 ml of formamide was introduced into a 100 ml three-necked flask, followed by 0.2 g of the product obtained in Example 7 and 0.8 g of the product obtained in Example 3. The mixture was thermostated to 95° C. and maintained under stirring at a constant temperature for 2.5 h, until the polymers had completely dissolved. The temperature was then reduced to 25° C., and the system was maintained under stirring overnight.

Sodium carbonate ($Na_2CO_3$— 68 mg) was then added, followed by CDI (340 mg dissolved in 1.4 ml of DMSO) after 0.5 h. The mixture was left under stirring for 24 h at 25° C.

The reaction was quenched by adding 40 ml of water, and the product was isolated by precipitation in acetone and subsequent decanting.

The crude reaction product was purified by several washes with acetone and methanol, each followed by vacuum filtration. The precipitate was dried under vacuum at room temperature for about 20 h.

Example 18: Synthesis of Crosslinked Sodium Hyaluronate Butyrate-Formate (80:20; MW: 25 kDa; $DS_{but}$:1.6: MW: 1500 kDa; $DS_{but}$:0.3; $DS_{for}$:0.01)

20 ml of formamide was introduced into a 100 ml three-necked flask, followed by 0.8 g of the product obtained in Example 9 and 0.2 g of the product obtained in Example 1. The mixture was thermostated to 95° C. and maintained under stirring at a constant temperature for 2.5 h, until the polymers had completely dissolved. The temperature was then reduced to 25° C., and the system was maintained under stirring overnight.

Sodium carbonate ($Na_2CO_3$— 75 mg) was then added, followed by CDI (372 mg dissolved in 1.4 ml of DMSO) after 0.5 h. The mixture was left under stirring for 24 h at 25° C.

The reaction was quenched by adding 40 ml of water, and the product was isolated by precipitation in acetone and subsequent decanting.

The crude reaction product was purified by several washes with acetone and methanol, each followed by vacuum filtration. The precipitate was dried under vacuum at room temperature for about 16 h.

Example 19: Synthesis of Crosslinked Sodium Hyaluronate Butyrate-Formate (20:80; MW: 25 kDa; $DS_{but}$:1.6: MW: 1500 kDa; $DS_{but}$:0.3; $DS_{for}$:0.01)

20 ml of formamide was introduced into a 100 ml three-necked flask, followed by 0.2 g of the product obtained in Example 9 and 0.8 g of the product obtained in Example 1. The mixture was thermostated to 95° C. and maintained under stirring at a constant temperature for 2.5 h, until the polymers had completely dissolved. The temperature was then reduced to 25° C., and the system was maintained under stirring overnight.

Sodium carbonate ($Na_2CO_3$— 70 mg) was then added, followed by CDI (3348 mg dissolved in 1.4 ml of DMSO) after 0.5 h. The mixture was left under stirring for 24 h at 25° C.

The reaction was quenched by adding 40 ml of water, and the product was isolated by precipitation in acetone and subsequent decanting.

The crude reaction product was purified by several washes with acetone and methanol, each followed by vacuum filtration. The precipitate was dried under vacuum at room temperature for about 20 h.

Example 20: Synthesis of Sodium Hyaluronate Butyrate-Formate (MW: 1500:300 kDa 80:20; $DS_{but}$:0.9; $DS_{for}$:0.02)

150 ml of formamide was introduced into a 1 l reactor followed by 6 g of sodium hyaluronate with a molecular weight of 1500 kDa and 1.5 g of sodium hyaluronate with a molecular weight of 300 kDa. The mixture was thermostated to 95° C. and maintained under stirring at a constant temperature for 1.5 h, until the polymers had completely dissolved. The temperature was reduced to 25° C. and the system was maintained under stirring overnight.

Sodium carbonate ($Na_2CO_3$— 0.6 g) was then added, followed by butyryl-imidazolide (5.7 g) after 0.5 h. The mixture was left under stirring for 1.5 h at 25° C.

The reaction was quenched with 65 ml of acidic water, and the product was isolated by precipitation with acetone and subsequent decanting.

The crude reaction product was purified by several washes with acetone and methanol, each followed by vacuum filtration. The precipitate was dried under vacuum at room temperature for about 18 h.

A 10 mg sample was solubilised in 0.8 ml of heavy water ($D_2O$) and transferred to an NMR tube.

After hydrolysis of the butyric and formic esters by adding NaOD (deuterated sodium hydroxide), the NMR spectrum exhibited a DS of 0.9 in butyric acid and 0.02 in formic acid.

Example 21: Synthesis of Crosslinked Sodium Hyaluronate Butyrate-Formate from Example 20+Carbonyldiimidazole (CDI)

20 ml of formamide and 2 g of the product obtained in Example 20 were introduced into two different 100 ml three-necked flasks (called A and B). The mixtures were thermostated to 95° C. and maintained under stirring at a constant temperature for 1 h, until the products had completely dissolved. The temperature was reduced to 25° C., and the systems were maintained under stirring overnight.

Dimethylaminopyridine (DMAP-263 mg, solubilised in 1.5 ml of formamide) was added to flask A, followed after 1 h by CDI (350 mg dissolved in 1.5 ml of DMSO). The mixture was left under stirring for 2 h at 25° C.

Dimethylaminopyridine (DMAP-263 mg, solubilised in 1.5 ml of FA) was added to flask B, and the mixture was left under stirring for 2 h at 25° C.

Mixture A was added to mixture B, and the system was left to react under stirring for about 4 h. The reaction was quenched with 70 ml of water, and the pH was adjusted from 10 to 7.5 by adding 10 ml of 0.5 M HCl.

The crude product was isolated by precipitation with acetone and purified by several washes with methanol, each followed by vacuum filtration. The precipitate was dried under vacuum at room temperature for about 16 h.

50 mg of sample was added to 5 ml of ultra-pure water (concentration 1% w/v); 24 h after mixing, the resulting gel, on rheology testing, gave G'=480 Pa and G"=70 Pa.

Example 22: Synthesis of Sodium Hyaluronate Butyrate-Formate (MW: 1500:300 kDa 20:80; $DS_{but}$:0.9; $DS_{for}$:0.02)+Cross-linking 150 ml of formamide was introduced into a 1 l reactor followed by 1.5 g of sodium hyaluronate with a molecular weight of 1500 kDa and 6 g of sodium hyaluronate with a molecular weight of 300 kDa. The mixture was thermostated to 95° C. and maintained under stirring at a constant temperature for 1.5 h, until the polymers had completely dissolved. The temperature was reduced to 25° C. and the system was maintained under stirring overnight.

Sodium carbonate ($Na_2CO_3$— 0.6 g) was then added, followed by butyryl-imidazolide (5.7 g) after 0.5 h. The mixture was left under stirring for 1.5 h at 25° C.

547.5 mg of sodium carbonate was then added and the mixture was left under stirring for 0.5 h, after which 2.6 g of CDI dissolved in 11 ml of dimethylsulphoxide was added.

After 24 h the product was precipitated by adding acetone to the crude reaction product.

The isolated crude product was purified by several successive washes with acetone and methanol, each followed by vacuum filtration. The precipitate was dried under vacuum at room temperature for about 10 h.

A 10 mg sample was solubilised in 0.8 ml of heavy water ($D_2O$) and transferred to an NMR tube.

After hydrolysis of the butyric and formic esters by adding NaOD (deuterated sodium hydroxide), the NMR spectrum exhibited a DS of 0.9 in butyric acid and 0.02 in formic acid.

Example 23: Synthesis of Sodium Hyaluronate Butyrate-Formate (MW: 1500:25 kDa 20:80; $DS_{but}$:0.9; $DS_{for}$:0.02)

150 ml of formamide was introduced into a 1 l reactor followed by 1.5 g of sodium hyaluronate with a molecular weight of 1500 kDa and 6 g of sodium hyaluronate with a molecular weight of 25 kDa. The mixture was thermostated to 95° C. and maintained under stirring at a constant temperature for 1.5 h, until the polymers had completely dissolved. The temperature was reduced to 25° C. and the system was maintained under stirring overnight.

Sodium carbonate ($Na_2CO_3$— 0.6 g) was then added, followed by butyryl-imidazolide (5.7 g) after 0.5 h. The mixture was left under stirring for 1.5 h at 25° C.

The reaction was quenched with 65 ml of acidic water, and the product was isolated by precipitation with acetone and subsequent decanting.

The crude reaction product was purified by several washes with acetone and methanol, each followed by vacuum filtration. The precipitate was dried under vacuum at room temperature for about 18 h.

A 10 mg sample was solubilised in 0.8 ml of heavy water ($D_2O$) and transferred to an NMR tube.

After hydrolysis of the butyric and formic esters by adding NaOD (deuterated sodium hydroxide), the NMR spectrum exhibited a DS of 0.9 in butyric acid and 0.02 in formic acid.

Example 24: Synthesis of Crosslinked Sodium Hyaluronate Butyrate-Formate from Example 23+Carbonyldiimidazole (CDI)

20 ml of formamide and 2 g of the product obtained in Example 23 were introduced into two different 100 ml three-necked flasks (called A and B). The mixtures were thermostated to 95° C. and maintained under stirring at a constant temperature for 1 h, until the products had completely dissolved. The temperature was reduced to 25° C., and the systems were maintained under stirring overnight.

Sodium carbonate ($Na_2CO_3$— 114.4 mg) was added to flask A, followed after 1 h by CDI (350 mg dissolved in 1.5 ml of DMSO). The mixture was left under stirring for 2 h at 25° C.

Sodium carbonate ($Na_2CO_3$— 114.4 mg) was added to flask B, and the mixture was left under stirring for 2 h at 25° C.

Mixture A was added to mixture B, and the system was left to react under stirring for about 4 h. The reaction was quenched with 70 ml of water, and the pH was adjusted from 10 to 7.5 by adding 0.5 M HCl.

The crude product was isolated by precipitation with acetone and purified by several washes with acetone and methanol, each followed by vacuum filtration. The precipitate was dried under vacuum at room temperature for about 16 h.

Example 25: Synthesis of Sodium Hyaluronate Butyrate-Formate (MW: 1500:25 kDa 80:20; $DS_{but}$:0.9; $DS_{for}$:0.02)+Cross-linking 150 ml of formamide was introduced into a 1 l reactor followed by 6.0 g of sodium hyaluronate with a molecular weight of 1500 kDa and 1.5 g of sodium hyaluronate with a molecular weight of 25 kDa. The mixture was thermostated to 95° C. and maintained under stirring at a constant temperature for 1.5 h, until the polymers had completely dissolved. The temperature was reduced to 25° C. and the system was maintained under stirring overnight.

Sodium carbonate ($Na_2CO_3$— 0.65 g) was then added, followed by butyryl-imidazolide (5.9 g) after 0.5 h. The mixture was left under stirring for 1.5 h at 25° C.

550.0 mg of sodium carbonate was then added and the mixture was left under stirring for 0.5 h, after which 2.7 g of CDI dissolved in 11 ml of dimethylsulphoxide was added.

After 24 h the crude reaction product was precipitated by adding acetone.

The isolated crude product was purified by several successive washes with acetone and methanol, each followed by vacuum filtration. The precipitate was dried under vacuum at room temperature for about 10 h.

A 10 mg sample was solubilised in 0.8 ml of heavy water ($D_2O$) and transferred to an NMR tube.

After hydrolysis of the butyric and formic esters by adding NaOD (deuterated sodium hydroxide), the NMR spectrum exhibited a DS of 0.9 in butyric acid and 0.02 in formic acid.

Example 26: Synthesis of Crosslinked Sodium Hyaluronate Butyrate-Formate (80:20; MW: 1500 kDa; $DS_{but}$:1.6 $DS_{for}$:0.03, MW: 300 kDa; $DS_{but}$:2.16; $DS_{for}$:0.02)

40 ml of formamide was introduced into a 250 ml three-necked flask, followed by 1.6 g of the product obtained in Example 3 and 0.4 g of the product obtained in Example 6. The mixture was thermostated to 95° C. and maintained under stirring at a constant temperature for 1 h, until the polymers had completely dissolved. The temperature was then reduced to 25° C., and the system was maintained under stirring overnight.

Sodium carbonate ($Na_2CO_3$— 122 mg) was then added, followed by CDI (252 mg dissolved in 1 ml of DMSO) after 0.75 h. The mixture was left under stirring for 24 h at 25° C.

The reaction was quenched by adding 80 ml of water, and the product was isolated by precipitation in acetone and subsequent filtration.

The crude reaction product was purified by several successive washes with acetone and methanol, each followed by vacuum filtration. The precipitate was dried under vacuum at room temperature for about 16 h.

Two swelling tests were conducted:

1. 100 mg of polymer was dissolved in 10 mM PBS pH 7.2 at a concentration of 2%. The sample obtained then underwent a sterilization cycle in the autoclave at 121° C. for 15 min. After being left to stand for 24 h, the rheological measurements were conducted.
2. 100 mg of polymer was dissolved in 10 ml water (concentration of 1%). After 24 h the gel was homogenized manually and rheological measurements were conducted.

The results are set out in Table 1 below.

TABLE 1

| | Viscosity (Pa*s) | G' (Pa) | G"(Pa) |
|---|---|---|---|
| 1 | 51.600 | 93 | 29 |
| 2 | 270.000 | 788 | 95 |

Moduli evaluated on SS at tau 1 Pa

Example 27: Synthesis of Crosslinked Sodium Hyaluronate Butyrate-Formate (MW: 1500 kDa; $DS_{but}$:1.6 $DS_{for}$:0.03)

40 ml of formamide was introduced into a 250 ml three-necked flask, followed by 2 g of the product obtained in Example 3. The mixture was thermostated to 95° C. and maintained under stirring at a constant temperature for 1 h, until the polymers had completely dissolved. The temperature was then reduced to 25° C., and the system was maintained under stirring overnight.

Sodium carbonate ($Na_2CO_3$— 124 mg) was then added, followed by CDI (258 mg dissolved in 1 ml of DMSO) after 0.75 h. The mixture was left under stirring for 24 h at 25° C.

The reaction was quenched by adding 80 ml of water, and the product was isolated by precipitation in acetone and subsequent filtration.

The crude reaction product was purified by several successive washes with acetone and methanol, each followed by vacuum filtration. The precipitate was dried under vacuum at room temperature for about 16 h.

Example 28: Synthesis of Crosslinked Sodium Hyaluronate Butyrate-Formate (MW: 300 kDa; $DS_{but}$:2.16; $DS_{for}$:0.02)

40 ml of formamide was introduced into a 250 ml three-necked flask, followed by 2 g of the product obtained in Example 6. The mixture was thermostated to 95° C. and maintained under stirring at a constant temperature for 1 h, until the polymers had completely dissolved. The temperature was then reduced to 25° C., and the system was maintained under stirring for 3 h.

Sodium carbonate ($Na_2CO_3$— 116 mg) was then added, followed by CDI (240 mg dissolved in 1 ml of DMSO) after 0.75 h. The mixture was left under stirring for 24 h at 25° C.

The reaction was quenched by adding 80 ml of water, and the product was purified by dialysis and recovered by freeze-drying.

Example 29 (Comparative): Mixture (80:20) of Crosslinked Sodium Hyaluronate Butyrate-Formate (MW: 1500 kDa; $DS_{but}$:1.6 $DS_{for}$:0.03) and Crosslinked Sodium Hyaluronate Butyrate-Formate (MW: 300 kDa; $DS_{but}$:2.1; $DS_{for}$:0.02)

1. 80 mg of the product of Example 27 and 20 mg deriving from Example 28 were dissolved in 10 mM PBS pH 7.2 at a concentration of 2%. The sample obtained then underwent a sterilization cycle in the autoclave at 121° C. for 15 min. After being left to stand for 24 h, the rheological measurements were conducted.
2. 80 mg of the product of Example 27 and 20 mg deriving from Example 28 were dissolved in 10 ml of water (concentration of 1%). After 24 h the gel was homogenized manually and rheological measurements were conducted. The results are set out in Table 2 below.

TABLE 2

| | Viscosity (Pa*s) | G' (Pa) | G" (Pa) |
|---|---|---|---|
| 1 | 3.200 | 6.4 | 7.6 |
| 2 | 8.7 | 9 | 16 |

Moduli evaluated on SS at tau 1 Pa

Example 30: Preparation of a Medical Device in the Form of a Syringe Containing 2.0 ml of a 2% w/v Hydrogel of the Crosslinked Product Obtained According to Example 26 and 0.3% w/v of Lidocaine 40 mg of crosslinked esterified polymer in powder form, obtained according to Example 26, was weighed in a sterile 2.5 ml syringe with 6 mg of lidocaine hydrochloride; 2.0 ml of an aqueous solution of 10 mM PBS buffer pH 7.2 was introduced into the syringe. The polymer was left to swell for 24 hours at room temperature. The syringe was then steam-sterilized in accordance with a standard cycle at 121° C. for 15 minutes in the autoclave. 24 h after sterilization, the resulting gel was extruded from the syringe and underwent rheological characterization.

The results are set out in Table 3 below.

TABLE 3

| | Viscosity (Pa*s) | G' (Pa) | G" (Pa) |
|---|---|---|---|
| 2 PBS 10 mM pH 7.2 | 30.000 | 82 | 28 |

Example 31: Preparation of a 2% w/v Hydrogel of the Crosslinked Product Obtained According to Example 26, Containing an Amino Acid 107 mg of crosslinked esterified polymer in powder form, obtained according to Example 26, was weighed in a sterile 10.0 ml vial; 5.0 ml of an aqueous solution of Ringer Lactate containing histidine at the concentration of 50 mM, with pH 7.0, was poured into the vial. The polymer was left to swell for 24 hours at room temperature. The sealed vial was then steam-sterilized in accordance with a standard cycle at 121° C. for 15 minutes in the autoclave. 30 days after sterilization the resulting gel underwent rheological characterization.

The results are set out in Table 4 below

TABLE 4

| | Viscosity (Pa*s) | G' (Pa) | G" (Pa) |
|---|---|---|---|
| 2% Ringer lactate - histidine 50 mM pH 7.0 | 89.500 | 130 | 35 |

Example 32: Formulation for Ophthalmic Use Starting with a Crosslinked Product Obtained According to Example 26

5 ml of water was introduced into a 10 ml vial, and 0.045 g of sodium chloride was dissolved in it. 0.025 g of crosslinked esterified polymer in powder form, obtained according to Example 26, was then added. The polymer was left to swell for 24 hours at room temperature. The sealed vial was then steam-sterilized in accordance with a standard cycle at 121° C. for 15 minutes in the autoclave.

Example 33: Topical Formulation Starting with a Crosslinked Product Obtained According to Example 26

| INCI name | Quantity % w/w |
|---|---|
| Aqua | 60.1 |
| Magnesium Aluminium silicate | 2 |
| Product of Example 26 | 0.2 |
| Betaine | 1 |
| Xylitol | 1 |
| Tocopheryl Acetate | 0.5 |
| D-Panthenol | 0.2 |
| Biotin | 0.05 |
| Phenoxyethanol, Capryloyl Glycol | 0.7 |
| Glycerine | 34.25 |

The invention claimed is:

1. A process for preparing crosslinked hyaluronic acid butyrate or crosslinked hyaluronic acid butyrate-formate or an acceptable salt thereof, the process comprising:

crosslinking hyaluronic acid butyrate or hyaluronic acid butyrate-formate or a pharmaceutically acceptable salt thereof in an organic solvent with a carboxyl group activating reagent and a base forming a reaction mixture, buffering said reaction mixture to a pH of 7.2; and obtaining said crosslinked hyaluronic acid butyrate or said crosslinked hyaluronic acid butyrate-formate or said acceptable salt thereof, wherein the hyaluronic acid butyrate or hyaluronic acid butyrate-formate or a pharmaceutically acceptable salt thereof is a mixture of a high molecular weight polysaccharide having a weight average molecular weight ranging between 1000 kDa and 10000 kDa and a low molecular weight polysaccharide having a weight average molecular weight ranging between 1 kDa and 900 kDa, and wherein the process comprises sterilizing in an autoclave at 121° C. for 15 minutes.

2. The process according to claim 1 wherein the low molecular weight polysaccharide has a weight average molecular weight ranging from 1 kDa to 500 kDa and the high molecular weight polysaccharide has a weight average molecular weight ranging from 1000 kDa to 6000 kDa.

3. The process according to claim 2 wherein the low molecular weight polysaccharide has a weight average molecular weight ranging from 50 kDa to 300 kDa and the high molecular weight polysaccharide has a weight average molecular weight ranging from 1000 kDa to 2000 kDa.

4. The process according to claim 1, wherein the high molecular weight polysaccharide and the low molecular weight polysaccharide are present in an 80:20 to 20:80 weight ratio.

5. The process according to claim 1, wherein the hyaluronic acid butyrate or the hyaluronic acid butyrate-formate or a pharmaceutically acceptable salt thereof has a degree of substitution ranging from 0.1 to 2.2.

6. The process according to claim 1, wherein the acceptable salt of hyaluronic acid butyrate or of hyaluronic acid butyrate-formate is sodium, potassium lithium or a quaternary ammonium salt.

7. The process according to claim 6 wherein the acceptable salt is the sodium salt.

8. The process according to claim 6, wherein said quaternary ammonium salt is tetrabutylammonium.

9. The process according to claim 1, wherein the organic solvent is selected from basic polar aprotic solvents selected from the group consisting of N,N-dimethylformamide, dimethylacetamide, dimethylsulphoxide, N-methylpyrrolidone and formamide.

10. The process according to claim 9 wherein the organic solvent is formamide.

11. The process according to claim 1 wherein the carboxyl group activating reagent is selected from the group consisting of carbonyl diimidazole, 1,1'-carbonyl-di-(1,2,4-triazole), 1,1'-oxalylimidazole, 1,1'-thiocarbonylimidazole, 1,1'-carbonyl bis(2-methylimidazole), N-hydroxysuccinimide, p-nitrophenol, p-nitrophenyl trifluoroacetate, 2-halo-N-alkylpyridine salts and acyl halides.

12. The process according to claim 11 wherein the carboxyl group activating reagent is carbonyl diimidazole.

13. The process according to claim 1, wherein the base is selected from inorganic bases selected from carbonates, bicarbonates and hydroxides of an alkaline or alkaline-earth metal, aromatic or aliphatic organic bases comprising at least one atom of trisubstituted nitrogen selected from such as pyridine or its homologues, basic amines selected from triethylamine, N-methyl-piperazine or dimethylaminopyridine, or the alkaline or alkaline-earth metal salt of an organic acid selected from sodium or potassium acetate.

14. The process according to claim 13 wherein the base is sodium carbonate or dimethylaminopyridine.

15. The process according to claim 13, wherein said hydroxides of an alkaline or alkaline-earth metal is selected from sodium, potassium or magnesium.

16. The process according to claim 13, wherein said homologue of pyridine is collidine.

17. The process according to claim 1, wherein the reaction mixture is kept at a temperature ranging between 20° C. and 30° C. for a period ranging between 4 and 24 hours.

18. Crosslinked hyaluronic acid butyrate or crosslinked hyaluronic acid butyrate-formate or an acceptable salt thereof obtained by the process according to claim 1.

19. A pharmaceutical or cosmetic formulation or medical device comprising crosslinked hyaluronic acid butyrate or crosslinked hyaluronic acid butyrate-formate or a pharmaceutically acceptable salt thereof according to claim 18, and at least one pharmaceutically acceptable excipient and/or carrier.

20. The pharmaceutical or cosmetic formulation or medical device according to claim 19 containing a local anesthetic.

21. The pharmaceutical or cosmetic formulation or medical device process according to claim 20, wherein said local anesthetic is lidocaine.

* * * * *